United States Patent [19]  [11] 4,418,233
Danz et al.  [45] Nov. 29, 1983

[54] REMOVAL OF IMPURITIES FROM VINYL CHLORIDE

[75] Inventors: Eckehard Danz, Ludwigshafen; Gerd Krome, Weisenheim, both of Fed. Rep. of Germany

[73] Assignee: BASF Aktiengesellschaft, Fed. Rep. of Germany

[21] Appl. No.: 377,970

[22] Filed: May 13, 1982

[30] Foreign Application Priority Data

Jun. 4, 1981 [DE] Fed. Rep. of Germany ....... 3122181

[51] Int. Cl.$^3$ ............................................. B01D 15/00
[52] U.S. Cl. .................................... 570/239; 210/660; 210/689
[58] Field of Search ................ 210/660, 689; 570/216, 570/239

[56] References Cited

U.S. PATENT DOCUMENTS 3,865,887 2/1975 Gordon ............................... 570/239

OTHER PUBLICATIONS

Monaghan, P. H. et al., "Characterization of Some Chromatographic Adsorbents", *Anal. Chem.*, vol. 22, No. 6 (Jun. 1950), pp. 811–813.

*Primary Examiner*—Ivars C. Cintins
*Attorney, Agent, or Firm*—Keil & Witherspoon

[57] ABSTRACT

Impurities are removed from vinyl chloride by passing it over finely divided calcium oxide.

5 Claims, No Drawings

REMOVAL OF IMPURITIES FROM VINYL CHLORIDE

The present invention relates to a process for removing impurities from vinyl chloride by passing it over an adsorbent.

Monomeric vinyl chloride for the preparation of polyvinyl chloride must fulfill high purity requirements. Thus, for example, hydrogen chloride contained in the vinyl chloride leads to undesirable discoloration of the polymer. Moreover, it is found that iron salts which lead to discoloration of the monomer are formed by corrosion if monomeric vinyl chloride is stored for a relatively long period, due to the presence of traces of hydrogen chloride and water.

Monomeric vinyl chloride is therefore usually purified by distillation before use. Hydrogen chloride and most of the water can be removed from the monomeric vinyl chloride by distillation, but because both hydrogen chloride and water (up to not more than 100 ppm) are present, it is necessary to use corrosion-resistant distillation columns and condensers. This type of purification of the monomer is therefore technically complicated.

In another process, hydrogen chloride is removed from monomeric vinyl chloride by washing the monomer in sodium hydroxide solution or potassium hydroxide solution. The vinyl chloride purified in this manner is then dried by being passed over finely divided sodium hydroxide or potassium hydroxide. The disadvantage of this process is that reaction of traces of hydrogen chloride which are still present with the sodium hydroxide or potassium hydroxide gives smeary by-products which are partly soluble in vinyl chloride. Such a process is therefore still not completely satisfactory.

It is an object of the present invention to provide a process for removing impurities from vinyl chloride, by passing it over an adsorbent, which does not have the disadvantages of the known processes.

We have found that this object is achieved by using finely divided calcium oxide as the adsorbent.

One advantage of the process is that iron salts can be removed from the monomeric vinyl chloride together with the water and hydrogen chloride. The fine-particled calcium oxide retains its geometric structure even after the adsorption, and does not disintegrate. Thus, the strength of the adsorbent is retained, and the pressure loss in the adsorber therefore remains constant. Th stoichiometric capacity of the calcium oxide can be utilized to the extent of more that 50%.

Calcium oxide in fine-particled form with an average particle diameter of from 0.5 to 5 mm is used as the adsorbent. The calcium oxide obtained by burning chalk is advantageously used. Liquid vinyl chloride is passed over the calcium oxide at from 20° to 70° C., in particular from 30° to 50° C., and under pressures of from 3.5 bar to 12 bar, in particular from 4 to 8 bar. The residence time in the adsorber in advantageously from 1.0 to 5.0 minutes, so that from 60 tonnes/hour to 12 tonnes/hour of vinyl chloride can be passed over 1 tonne of calcium oxide.

The adsorber is advantageously a cylindrical reaction vessel filled with the finely divided calcium oxide and the vinyl chloride is advantageously passed downwards through the adsorber.

We have found, surprisingly, that the vinyl chloride purified in this manner can be used directly for polymerization, to give vinyl chloride polymers containing no discoloring impurities.

EXAMPLE

A cylindrical adsorber 146 l in volume and 88 cm in height is filled completely with calcium oxide having a particle diameter of 0.3 to 1.5 cm and a bulk density of 1 kg/l.

The amounts of vinyl chloride given in the accompanying table are passed through the adsorber. The contents of hydrogen chloride and water before and after the adsorptive treatment are also given in the table.

TABLE

| Experiment | Amount of vinyl chloride (tonnes/hour) through the adsorber | HCl upstream of the adsorber ppm | $H_2O$ upstream of the adsorber ppm | HCl downstream of the adsorber ppm | $H_2O$ downstream of the adsorber ppm |
|---|---|---|---|---|---|
| I | 1 | 2,400 | | 800 | |
| II | 2 | 2,400 | | 930 | |
| III | 3.0 | 22 | 20-25 | 2 | 10 |
| IV | 1.5 | 18 | 20-25 | 1 | 10 |
| V | 1.5 | 14 | 20-25 | 1 | 10 |
| VI | 1.5 | 25 | 20-25 | 1 | 10 |
| VII | 5.0 | 20 | 20-25 | 2 | 10 |

We claim:

1. A process for removing hydrogen chloride and water as impurities from vinyl chloride which comprises: passing liquid vinyl chloride over finely divided calcium oxide at a temperature of from 20° to 70° C. whereby the impurities are absorbed on the calcium oxide.

2. The process of claim 1 wherein a temperature of from 30° to 50° C. is employed.

3. The process of claim 2 wherein the absorption takes place at a pressure of from 4 to 8 bar.

4. The process of claim 1 wherein the absorption is carried out at a pressure of from 3.5 to 12 bar.

5. The process of claim 1 wherein the finely divided calcium oxide has a mean particle diameter of from 0.5 to 5 mm.

* * * * *